(12) United States Patent
Lau et al.

(10) Patent No.: US 7,338,928 B2
(45) Date of Patent: Mar. 4, 2008

(54) SYSTEM FOR RELEASING ENCAPSULATED ACTIVE INGREDIENTS

(75) Inventors: Willie Lau, Lower Gwynedd, PA (US); Curtis Schwartz, Ambler, PA (US); Adi Shefer, East Brunswick, NJ (US)

(73) Assignee: Rohm and Haas Company, Philadelphia, PA (US)

( * ) Notice: Subject to any disclaimer, the term of this patent is extended or adjusted under 35 U.S.C. 154(b) by 399 days.

(21) Appl. No.: 11/003,869

(22) Filed: Dec. 3, 2004

(65) Prior Publication Data

US 2005/0153862 A1    Jul. 14, 2005

Related U.S. Application Data

(60) Provisional application No. 60/528,922, filed on Dec. 11, 2003.

(51) Int. Cl.
| | |
|---|---|
| *C11D 17/06* | (2006.01) |
| *C11D 3/50* | (2006.01) |
| *C11D 3/37* | (2006.01) |
| *A61K 8/11* | (2006.01) |
| *A61K 9/51* | (2006.01) |

(52) U.S. Cl. ............... 510/441; 510/101; 510/349; 510/367; 510/394; 510/475; 424/401; 424/490; 424/494; 424/497; 424/498; 512/4

(58) Field of Classification Search ........ 510/349, 510/101, 441, 475, 367, 394; 424/401, 490, 424/494, 497, 498; 512/4
See application file for complete search history.

(56) References Cited

U.S. PATENT DOCUMENTS

| | | | |
|---|---|---|---|
| 3,975,280 A * | 8/1976 | Hachmann et al. | ..... 252/186.31 |
| 4,303,679 A | 12/1981 | Raccach | |
| 4,663,068 A | 5/1987 | Hagemann et al. | |
| 5,051,222 A | 9/1991 | Marten et al. | |
| 5,312,863 A | 5/1994 | Van Rheenen et al. | |
| 5,521,266 A | 5/1996 | Lau | |
| 5,556,835 A | 9/1996 | Inaoka et al. | |
| 5,596,051 A * | 1/1997 | Jahns et al. | ............ 526/73 |
| 6,375,983 B1 * | 4/2002 | Kantor et al. | ............ 424/489 |
| 6,528,073 B2 * | 3/2003 | Roulier et al. | ............ 424/401 |
| 6,558,706 B2 * | 5/2003 | Kantor et al. | ............ 424/489 |
| 6,770,285 B2 | 8/2004 | Keenan et al. | |
| 6,979,440 B2 * | 12/2005 | Shefer et al. | ............ 424/78.02 |
| 7,053,034 B2 * | 5/2006 | Shefer et al. | ............ 510/349 |
| 7,119,060 B2 * | 10/2006 | Shefer et al. | ............ 510/519 |
| 2001/0038829 A1 | 11/2001 | Hasebe et al. | |

FOREIGN PATENT DOCUMENTS

| | | |
|---|---|---|
| EP | 0 441512 | 5/1994 |
| EP | 0545556 | 7/1997 |
| EP | 1111034 | 6/2001 |
| JP | 1998-316082 | 11/1998 |
| JP | 2000-279446 | 9/2000 |
| WO | WO/0140430 | 7/2001 |

* cited by examiner

*Primary Examiner*—Lorna M. Douyon

(57) ABSTRACT

The present invention relates to a controlled release system that can be incorporated in cosmetic, personal care, and household products to effectively encapsulate wide range of active ingredients and sensory markers and release them in response to moisture or over an extended period of time. The controlled release system of the present invention consists of oil absorbing polymer nanospheres coated with water sensitive surface active polymers.

5 Claims, No Drawings

SYSTEM FOR RELEASING ENCAPSULATED ACTIVE INGREDIENTS

CROSS REFERENCE TO RELATED PATENT APPLICATIONS

This is a non-provisional patent application of co-pending U.S. provisional patent application Ser. No. 60/528,222 filed Dec. 11, 2003.

The present invention relates to a system and process for releasing one or more encapsulated sensory markers and active ingredients for an extended period of time. In particular, the invention is directed to water sensitive, surface active coatings and one or more oil absorbing polymers that encapsulate one or more active ingredients and sensory markers, including fragrances. In response to contact of the coatings with water, the active ingredients are released to an environment of use and remain in proximity to the environment over an extended period of time. The system further provides moisture triggered release of active ingredients included in cosmetic, personal care, and household products.

Compositions incorporating one or more sensory markers in the form of a perfume provide a perceived benefit to consumers in that articles treated with the compositions are more aesthetically pleasing to the consumer, including cases where the perfume imparts a pleasant fragrance to the articles treated therewith. For example, in rinse dosed fabric softeners, fragrance is a desirable component since it imparts to the user a perception of freshness. However, the amount of perfume delivered, transferred or carried over to environments (e.g. aqueous laundry bath including fabrics) where the compositions are released onto specific articles (e.g. fabrics) is often marginal. Industry, therefore, has long searched for an effective perfume delivery system for use in detergent products which provides long-lasting, storage-stable fragrance to an article, as well as provides controlled and sustained release of fragrance to an environment of use.

International Patent Publication No. WO/01 40430 A1 discloses a delivery system comprising perfume loaded into porous carriers such as zeolite particles, by coating said loaded carrier particles with a hydrophobic oil and thereafter encapsulating the oil-coated perfume-loaded carrier particles with a water-soluble or water-dispersible, but oil-insoluble, material, such as starch or modified starch. The system claims to deposit enough perfume on fabrics to deliver a noticeable odor benefit even after the fabrics are dry. However, use of zeolites as perfume carriers in such delivery systems, often does not result in delivery of perfume in a sustained manner onto, laundered, softened and cleaned articles. Porous materials such as zeolites release perfume rapidly upon contact with water, thus reducing the amount of perfume residing in the particles upon deposition on articles surface (e.g. fabric surface of an article from the wash liquor or rinse). In addition, it is established in the prior art that when such particles are employed in dry products, e.g. granular laundry powders, the particles typically demonstrate a limited useful lifetime. If the liquid loaded in the porous zeolite carrier is perfume, the perfumery ability is lost upon storage, with the perfume evaporating from the delivery system and slowly being released from the encapsulating agent to the atmosphere or surrounding laundry powder base. Once released, there is no mechanism in a dry product for returning the perfume to the particle. This effect is disadvantageous in products intended for use in laundry applications for example, where it is desirable to deliver fragrance to a fabric surface of an article upon washing, and a lingering and prolonged fragrance during the storage of laundered articles.

Inventors have discovered a system for releasing one or more encapsulated active ingredients comprising one or more oil absorbing polymers and a coating comprising one or more water sensitive, surface active polymers to encapsulate the active ingredients. Release of the ingredients is triggered in response to water contacting the coating that encapsulates the active ingredients. The delivery of active ingredients and fragrances of the system of the invention obviates problems associated with delivery systems in the prior art. Moreover, the invention provides a system for releasing actives in cosmetic, personal care, and household products to an environment of use over an extended period of time, while the released actives remain in close proximity to the environment they were released to.

Accordingly, the invention provides a system for releasing one or more active ingredients from a composition comprising one or more oil absorbing polymers and a coating comprising one or more water sensitive, surface active polymers; wherein the active ingredients are encapsulated using a combination of (a) and (b) and are released upon contact of the coating with water.

The invention provides a process for preparing a system for releasing one or more active ingredients from a composition comprising the steps of: (a) incorporating one or more active ingredients in nano-particles comprising one or more oil-absorbing polymers; and (b) encapsulating the nano-particles using one or more said water sensitive, surface active polymers as a triggered release coating.

As used herein, the term "(meth)acrylic" refers to either the corresponding acrylic or methacrylic acid and derivatives; similarly, the term "alkyl (meth)acrylate" refers to either the corresponding acrylate or methacrylate ester. As used herein, all percentages referred to will be expressed in weight percent (%), based on total weight of polymer or composition involved, unless specified otherwise.

The term "environment of use" refers to any solid substrate including skin, hair, fabric and textiles that the active ingredients are released to using the triggered release system of the invention. The term "contact with water" refers to water in the form of moisture, humidity, vapor, aqueous solutions and aqueous dispersions that contacts the triggered release system of the invention.

Polymers usefully employed in accordance with the invention are aqueous emulsion polymers prepared from water insoluble, hydrophobic monomers and are described in U.S. Pat. No. 5,521,266 and European Patent Publication No. EP 1 209 213 A1. As used herein, the term "water soluble", as applied to monomers, indicates that the monomer has a solubility of at least 1 gram per 100 grams of water, preferably at least 10 grams per 100 grams of water and more preferably at least about 50 grams per 100 grams of water. "Hydrophobic monomers" refer to monoethylenically unsaturated monomers which have low or very low water solubility under the conditions of emulsion polymerization, as described in U.S. Pat. No. 5,521,266. As used herein, monomers having "low water solubility" or "very low water solubility" refers to monoethylenically unsaturated monomers having a water solubility at 25-50° C. of no greater than 200 millimoles/liter water or 50 millimoles/liter water, respectively, and the hydrophobic monomers employed in this invention are monomers having low water solubility.

According to one embodiment, the oil absorbing polymer is prepared as a terpolymer, wherein monomer A is a residue of (meth)acrylic acid, monomer B is a residue selected from $C_8$-$C_{20}$ alkyl (meth)acrylates, and monomer C is residue selected from $C_1$-$C_{24}$ alkyl (meth)acrylates. The terpolymer also may include initiators and chain transfer residues, respectively. The terpolymer is prepared from relatively high levels (as wt. %) of hydrophobic monomers and relatively low levels (as wt. %) of ionic monomers in the form of (meth)acrylic acid or acrylic acid. The terpolymer includes from 80% to 98% by weight of a combination of one or more hydrophobic monomers in the form of $C_4$-$C_{24}$ alkyl (meth) acrylates and from 0.01% to 20% by weight of one or more ionic monomers.

According to a separate embodiment, a cross-linking polyethylenically unsaturated monomer is used in making the oil absorbing polymer. As used herein, the terms "polyethylenically" and "multi-ethylenically" refer to monomers having a plurality of ethylenically unsaturated groups.

"Ionic monomers" refer to monoethylenically unsaturated monomers which are water soluble under the conditions of emulsion polymerization, as described in U.S. Pat. No. 4,880,842.

The weight average molecular weight of the backbone, as measured on the polymer product after exhaustive hydrolysis, consisting of polymerized units of A, B and C, ranges from 1,000 to 100,000. Weight average molecular weights were measured using gel permeation chromatography (GPC) with styrene as a standard and are expressed as weight average molecular weight.

The oil-absorbing emulsion polymers of the present invention have an average particle diameter that ranges from 20 nm to 1000 nm, including from 100 nm to 600 nm. Particle sizes herein are those determined using a Brookhaven Model BI-90 particle sizer manufactured by Brookhaven Instruments Corporation, Holtsville N.Y., and polymer particle diameters are reported as "effective diameter.

Oil absorbing polymers are prepared by free radical polymerization of hydrophobic and ionic monomers using conventional solution, suspension and emulsion polymerization processes, including those processes disclosed in U.S. Pat. Nos. 4,427,836; 4,469,825; 4,594,363; 4,677,003; 4,910,229; 4,920,160; 5,157,084; 5,521,266 and European Patent Nos. EP 0 267 726; EP 0 331 421, EP 0 915 108 and EP 1 209 213 A1.

According to one embodiment, the oil absorbing polymers are prepared by emulsion polymerization. Emulsion polymerization techniques for preparing aqueous dispersions of polymeric particles from ethylenically unsaturated monomers are well known in the polymer art. Single and multiple shot batch emulsion processes can be used, as well as continuous emulsion polymerization processes. In addition, if desired, a monomer mixture can be prepared and added gradually to the polymerization vessel. Similarly, the monomer composition within the polymerization vessel can be varied during the course of the polymerization, such as by altering the composition of the monomer being fed into the polymerization vessel. Both single and multiple stage polymerization techniques can be used. The polymer particles can be prepared using a seed polymer emulsion to control the number of particles produced by the emulsion polymerization as is known in the art. The particle size of the polymer particles can be controlled by adjusting the initial surfactant charge as is known in the art.

Aggregation of the polymer particles can be discouraged by inclusion of a micelle-forming, stabilizing surfactant in the polymerization mix. In general, the growing core particles are stabilized during emulsion polymerization by one or more surfactants, at least one of said surfactants being a non-ionic or amphoteric surfactant or mixtures thereof. These types of surfactants are well known in the emulsion polymerization art. Many examples of suitable surfactants are given in McCutchen's Detergents and Emulsifiers (MC Publishing Co., Glen Rock, N.J.), published annually. Other types of stabilizing agents, such as protective colloids, can also be used.

Examples of suitable anionic surfactants include the ammonium, alkali metal, alkaline earth metal, and lower alkyl quaternary ammonium softs of sulfosuccinates such as di(C7-C25) alkylsulfosuccinate; sulfates such as the higher fatty alcohol sulfates, for example, lauryl sulfate; sulfonates including aryl sulfonates, alkyl sulfonates, and the alkylaryl sulfonates, for example, isopropylbenzene sulfonate, isopropylnaphthalene sulfonate and N-methyl-N-palmitoyltaurate, isothionates such as oleyl isothionate; and the like. Additional examples include the alkylarylpoly(ethyleneoxy) ethylene sulfates, sulfonates and phosphates, such as t-octylphenoxypoly(ethylenoxy)ethylene sulfates and nonylphonoxy-poly(ethyleneoxy)ethylene phosphates, either having 1 to 7 oxyethylene units.

Examples of suitable non-ionic surfactants include poly (oxyalkylene) alkyphenol ethers, poly(oxyalkylene) alkyl ethers, poly(oxyalkylene) esters of fatty acids, polyethyleneoxidepolypropyleneoxide block copolymers, and the like.

Examples of suitable cationic surfactants include quaternary alkyl ammonium halides, phosphates, acetates, nitrates, sulfates; polyoxyalkyleneamines, poly(ethyleneoxide) amine, polyoxyalkylamine oxides, substituted imidazoline of alkyl fatty acids, alkylbenzyldimethylammonium halides, and alkyl pyridinium halides.

Examples for suitable amphoteric surfactants include imidiazoline derived amphotefics, as described in U.S. Pat. No. 5,312,863, wherein R is selected from the group consisting of straight and branched chain fatty acids and where the alkylene group has 8 to 20 carbon atoms; wherein R1 is selected from: —((CH2)x O)y —R' where x=2 and 3, y=0 to 6, R'=H, straight and branched chain fatty acids, and alcohols having 2 to 12 carbon atoms; and wherein R2 is selected from the group consisting of branched, straight chain aliphatic and aromatic carboxylic acids, sulfonic acids, phosphoric acids where the alkylene group has 1 to 18 carbon atoms. Other carboxybetaines, sulfatobetaines, sulfitobetaines, sulfobetaines, phosphoniobetaines, N-alkylamino acids and the like are also suitable.

In emulsion polymerization an aqueous polymerization medium is employed. The aqueous medium includes water and can include soluble inorganic salts, non-reactive water-miscible co-solvents such as lower alkanols and polyols, buffering agents, soluble and dispersible polymeric materials including protective colloids, and thickening and suspending agents such as polyvinyl alcohol, methoxycellulose, and hydroxyethylcellulose.

Active ingredients usefully employed in the triggered release system of the invention include oils, oil soluble compounds, water soluble compounds, water insoluble compounds, hydrophobic compounds, flavors, fragrances, perfumes, fabric softeners, bleaches and detergents. Other suitable active ingredients are active ingredients used in cosmetics, cleaners, detergents, personal care products and pharmaceuticals.

Fragrances can be included in the controlled system of the present invention. The fragrances that can be encapsulated in the system of the present invention can be any odoriferous material and can be selected according to the desires of the fragrance creator. In general terms, such fragrance materials are characterized by a vapor pressure below atmospheric pressure at ambient temperatures. The high boiling perfume materials employed herein will most often be solids at ambient temperatures, but also can include high boiling liquids. A wide variety of chemicals are known for perfumery and flavor uses, including materials such as aldehydes, ketones, esters, and the like. More commonly, naturally occurring plant and animal oils and exudates comprising complex mixtures of various chemical components are known for use as fragrances can be used herein. Fragrances useful for the present invention can be a single aroma chemical, relatively simple in their composition, or can comprise highly sophisticated, complex mixtures of natural and synthetic chemical components, all chosen to provide any desired odor.

Suitable fragrance which can be used in the present invention include, for example, high boiling components of woody/earthy bases containing exotic materials such as sandalwood oil, civet, patchouli oil, and the like. The perfumes herein can be of a light, floral fragrance, such as for example, high boiling components of rose extract, violet extract, and the like. The perfumes herein can be formulated to provide desirable fruity odors, such as for example lime, lemon, orange, and the like. The perfume can be any material of appropriate chemical and physical properties which exudes a pleasant or otherwise desirable odor when applied to fabrics. Perfume materials suitable for use in the present invention are described more fully in S. Arctander, Perfume Flavors and Chemicals, Vols. I and II, Aurthor, Montclair, N.J. and the Merck Index, 8th Edition, Merck & Co., Inc. Rahway, N.J., both references being incorporated herein by reference.

As is well known, a perfume normally consists of a mixture of a number of perfumery materials, each of which has a fragrance. The number of perfumery materials in a perfume is typically ten or more. The range of fragrant materials used in perfumery is very wide; the materials come from a variety of chemical classes, but in general are water-insoluble oils. In many instances, the molecular weight of a perfumery material is in excess of 150, but does not exceed 3000.

Perfumes used in the present invention include mixtures of conventional perfumery materials. Suitable perfumes and fragrances include: acetyl cedrene, 4-acetoxy-3-pentyltetrahydropyran, 4-acetyl-6-t-butyl-1,1-dimethylindane, available under the trademark "CELESTOLIDE", 5-acetyl-1,1,2,3,3,6-hexamethylindane, available under the trademark "PHANTOLIDE", 6-acetyl-1-isopropyl-2,3,3,5-tetramethylindane, available under the trademark "TRASEOLIDE", alpha-n-amylcinnamic aldehyde, amyl salicylate, aubepine, aubepine nitrile, aurantion, 2-t-butylcyclohexyl acetate, 2-t-butylcyclohexanol, 3-(p-t-butylphenyl)propanal, 4-t-butylcyclohexyl acetate, 4-t-butyl-3,5-dinitro-2,6-dimethyl acetophenone, 4-t-butylcyclohexanol, benzoin siam resinoids, benzyl benzoate, benzyl acetate, benzyl propionate, benzyl salicylate, benzyl isoamyl ether, benzyl alcohol, bergamot oil, bornyl acetate, butyl salicylate, carvacrol, cedar atlas oil, cedryl methyl ether, cedryl acetate, cinnamic alcohol, cinnamyl propionate, cis-3-hexenol, cis-3-hexenyl salicylate, citronella oil, citronellol, citronellonitrile, citronellyl acetate, citronellyloxyacetaldehyde, cloveleaf oil, coumarin, 9-decen-1-ol, n-decanal, n-dodecanal, decanol, decyl acetate, diethyl phthalate, dihydromyrcenol, dihydromyrcenyl formate, dihydromyrcenyl acetate, dihydroterpinyl acetate, dimethylbenzyl carbinyl acetate, dimethylbenzylcarbinol, dimethylheptanol, dimethyloctanol, dimyrcetol, diphenyl oxide, ethyl naphthyl ether, ethyl vanillin, ethylene brassylate, eugenol, geraniol, geranium oil, geranonitrile, geranyl nitrile, geranyl acetate, 1,1,2,4,4,7-hexamethyl-6-acetyl-1,2,3,4-tetrahydronaphthalene, available under the trademark "TONALID", 1,3,4,6,7,8-hexahydro-4,6,6,7,8,8-hexamethylcyclopenta-2-benzopyran, available under the trademark "GALAXOLIDE", 2-n-heptylcyclopentanone, 3a,4, 5, 6, 7, 7a-hexahydro-4,7-methano-(3)H-inden-6-ylpropionate, available under the trademark "FLOROCYCLENE", 3a,4, 5,6,7, 7a-hexahydro-4,7-methano-[(3)H-inden-6-yl]acetate, available under the trademark "JASMACYCLENE", 4-(4'-hydroxy-4'-methylpentyl)-3-cyclohexenecarbaldehyde, alpha-hexylcinammic aldehyde, heliotropin, Hercolyn D, hexyl aldone, hexyl cinnamic aldehyde, hexyl salicylate, hydroxycitronellal, i-nonyl formate, 3-isocamphylcyclohexanol, 4-isopropylcyclohexanol, 4-isopropylcyclohexyl methanol, indole, ionones, irones, isoamyl salicylate, isoborneol, isobornyl acetate, isobutyl salicylate, isobutylbenzoate, isobutylphenyl acetate, isoeugenol, isolongifolanone, isomethyl ionones, isononanol, isononyl acetate, isopulegol, lavandin oil, lemongrass oil, linalool, linalyl acetate, LRG 201, 1-menthol, 2-methyl-3-(p-isopropylphenyl) propanal, 2-methyl-3-(p-t-butylphenyl)propanal, 3-methyl-2-pentyl-cyclopentanone, 3-methyl-5-phenyl-pentanol, alpha and beta methyl naphthyl ketones, methyl ionones, methyl dihydrojasmonate, methyl naphthyl ether, methyl 4-propyl phenyl ether, Mousse de chene Yugo, Musk ambrette, myrtenol, neroli oil, nonanediol-1,3-diacetate, nonanol, nonanolide-1,4, nopol acetate, 1,2,3,4,5,6,7,8-octahydro-2, 3,8,8-tetramethyl-2-acetyl-naphthalene, available under the trademark "ISO-E-SUPER", octanol, Oppoponax resinoid, orange oil, p-t-amylcyclohexanone, p-t-butylmethylhydrocinnamic aldehyde, 2-phenylethanol, 2-phenylethyl acetate, 2-phenylpropanol, 3-phenylpropanol, para-menthan-7-ol, para-t-butylphenyl methyl ether, patchouli oil, pelargene, petitgrain oil, phenoxyethyl isobutyrate, phenylacetaldehyde diethyl acetal, phenylacetaldehyde dimethyl acetal, phenylethyl n-butyl ether, phenylethyl isoamyl ether, phenylethylphenyl acetate, pimento leaf oil, rose-d-oxide, Sandalone, styrallyl acetate, 1,1,4,4-tetramethyl-6-acetyl-7-ethyl-1,2,3,4-tetrahydronaphthalene, available under the trademark "VERSALIDE", 3,3,5-trimethyl hexyl acetate, 3,5,5-trimethylcyclohexanol, terpineol, terpinyl acetate, tetrahydrogeraniol, tetrahydrolinalool, tetrahydromuguol, tetrahydromyrcenol, thyme oil, trichloromethylphenylcarbinyl acetate, tricyclodecenyl acetate, tricyclodecenyl propionate, 10-undecen-1-al, gamma undecalactone, 10-undecen-1-ol, undecanol, vanillin, vetiverol, vetiveryl acetate, vetyvert oil, acetate and propionate esters of alcohols in the list above, aromatic nitromusk fragrances indane musk fragrances isochroman musk fragrances macrocyclic ketones, macrolactone musk fragrances and tetralin musk fragrances. Other suitable examples of fragrances and perfumes are described in European Patent Publication EP 1 111 034 A1.

Perfumes frequently include solvents or diluents, for example: ethanol, isopropanol, diethylene glycol monoethyl ether, dipropylene glycol, diethyl phthalate and triethyl citrate.

Perfumes which are used in the invention may, if desired, have deodorant properties as disclosed in U.S. Pat. No. 4,303,679, U.S. Pat. No. 4,663,068 and European Patent Publication EP 0 545 556 A1.

Absorption of perfume can be enhanced by choosing perfumery materials with a hydrophobic character or mixing a hydrophobic oil into the perfume. Suitable examples of hydrophobic oils which can enhance perfume uptake include: dibutylphthalate, alkane mixtures such as isoparaffin and di(C8-C10 alkyl) propylene glycol diester.

Water-sensitive, surface active polymers for coating the oil absorbing polymer nanospheres of the present invention comprise water soluble and water dispersible natural and synthetic polymers and copolymers, starch derivatives, polysaccharides, hydrocolloids, natural gums, proteins, and mixtures thereof.

Examples of synthetic water sensitive polymers which are useful for the invention include polyvinyl pyrrolidone, water soluble celluloses, polyvinyl alcohol, ethylene maleic anhydride copolymer, methylvinyl ether maleic anhydride copolymer, acrylic acid copolymers, anionic polymers of methacrylic acid and methacrylate, cationic polymers with dimethyl-aminoethyl ammonium functional groups, polyethylene oxides, water soluble polyamide or polyester.

Examples of water soluble hydroxyalkyl and carboxyalkyl celluloses include hydroxyethyl and carboxymethyl cellulose, hydroxyethyl and carboxyethyl cellulose, hydroxymethyl and carboxymethyl cellulose, hydroxypropyl carboxymethyl cellulose, hydroxypropyl methyl carboxyethyl cellulose, hydroxypropyl carboxypropyl cellulose, hydroxybutyl carboxymethyl cellulose, and the like. Also useful are alkali metal salts of these carboxyalkyl celluloses, particularly and preferably the sodium and potassium derivatives.

Polyvinyl alcohol useful in the practice of the invention is partially and fully hydrolyzed polyvinyl acetate, termed "polyvinyl alcohol" with polyvinyl acetate as hydrolyzed to an extent, also termed degree of hydrolysis, of from about 75% up to about 99%. Such materials are prepared by means of any of Examples I-XIV as described in U.S. Pat. No. 5,051,222.

A polyvinyl alcohol usefully employed in the present invention is Mowiol® 3-83, having a molecular weight of about 14,000 daltons (Da) and degree of hydrolysis of about 83%, Mowiol® 3-98 and a fully hydrolyzed (98%) polyvinyl alcohol having a molecular weight of 16,000 daltons (Da) commercially available from Gehring-Montgomery, Inc. of Warminister Pa. Other suitable polyvinyl alcohols are: AIRVOL® 205, having a molecular weight of about 15,000-27,000 Da and degree of hydrolysis of about 88%, and VINEX® 1025, having molecular weight of 15,000-27,000 Da degree of hydrolysis of about 99% and commercially available from Air Products & Chemicals, Inc. of Allentown, Pa.; ELVANOL® 51-05, having a molecular weight of about 22,000-26,000Da and degree of hydrolysis of about 89% and commercially available from the Du Pont Company, Polymer Products Department, Wilmington, Del.; ALCOTEX® 78 having a degree of hydrolysis of about 76% to about 79%, ALCOTEX® F88/4 having a degree of hydrolysis of about 86% to about 88% and commercially available from the Harlow Chemical Co. Ltd. of Templefields, Harlow, Essex, England CM20 2BH; and GOHSENOL® GL-03 and GOHSENOL® KA-20 commercially available from Nippon Gohsei K.K., The Nippon Synthetic Chemical Industry Co., Ltd., of No. 9-6, Nozaki Cho, Kita-Ku, Osaka, 530 Japan.

Suitable polysaccharides are polysaccharides of the nonsweet, coloidally-soluble types, such as natural gums, for example, gum arabic, starch derivates, dextrinized and hydrolyzed starches, and the like. A suitable polysaccharide is a water dispersible, modified starch commercially available as Capule®, N-Lok®, commercially available from the National Starch and Chemical Company of Bridgewater, N.J.; Pure-Cote™, commercially available from the Grain Processing Corporation of Muscatine, Iowa. In the preferred embodiment the natural gum is a gum arabic, commercially available from TIC Gums Inc. Belcamp, Midland. Suitable hydrocolloids are xanthan, maltodextrin, galactomanan or tragacanth, preferably maltodextrins such as Maltrin™ M100, and Maltrin™ M150, commercially available from the Grain Processing Corporation of Muscatine, Iowa.

The triggered release system of the present invention includes one or more active ingredients encapsulated in one or more oil absorbing polymer nanospheres coated with one or more water sensitive surface active polymers. The release rate of the active ingredients including sensory markers from the oil absorbing polymer nanospheres can be further sustained by mixing the active ingredients and sensory markers with solid hydrophobic materials, prior to encapsulating them in the oil absorbing polymer nanospheres.

Other hydrophobic materials are included in the triggered release system of the invention. Considerations in the selection of other hydrophobic materials incorporated in the oil absorbing polymer nanospheres to the sensory markers and active ingredients include good barrier properties to the sensory markers and active ingredients, low toxicity and irritancy, stability, integrity, and compatibility with the sensory markers and the active agents of interest. Suitable wax materials for the compositions and devices of the present invention are inert nontoxic materials with a melting point range between about 30 degrees C. and about 90 degrees C. and penetration point of about 1 to about 10. Examples of wax materials include natural waxes, synthetic waxes and mixtures thereof. Suitable waxes also include natural, regenerated, or synthetic food approved waxes including animal waxes such as beeswax, vegetable waxes such as carnauba, candelilla, sugar cane, rice bran, and bayberry wax, mineral waxes such as petroleum waxes including paraffin and microcrystalline wax, and mixtures thereof.

Other wax materials that are known to those skilled in the art and suitable materials as described in "Industrial Waxes" Vol. I and II, by Bennett F.A.I.C., published by Chemical Publishing Company Inc., 1975 and Martindale, "The Extra Pharmacopoeia", The Pharmaceutical Press, $28^{th}$ Edition pp. 1063-1072,1982 can be used in the present invention.

Other suitable fat (hydrophobic) materials and/or glyceride materials which can be used in the present invention include, but are not limited to, the following classes of lipids: mono-, di and triglycerides, phospholipids, sphingolipids, cholesterol and steroid derivatives, terpenes and vitamins. Examples of solid fat materials which can be used in the present invention, include solid hydrogenated castor and vegetable oils, hard fats, and mixtures thereof. Other fat materials which can be used, include triglycerides of food grade purity, which can be produced by synthesis or by isolation from natural sources. Natural sources can include animal fat or vegetable oil, such as soy oil, as a source of long chain triglycerides (LCT). Other triglycerides suitable for use in the present invention are composed of a majority of medium length fatty acids (C10-C18), denoted medium chain triglycerides (MCT). The fatty acid moieties of such triglycerides can be unsaturated or polyunsaturated and mixtures of triglycerides having various fatty acid material. Steroids which can be used include as fat materials, but are not limited to, cholesterol, cholesterol sulfate, cholesterol hemisuccinate, 6-(5-cholesterol 3 beta-yloxy) hexyl6-amino-6-deoxy-1-thio-alpha-D-galactopyranoside, 6-(5-cholesten-3 beta-tloxy)hexyl-6-amino-6-deoxyl-1-thio-alpha-D mannopyranoside and cholesteryl)$_4$'-trimethyl 35 ammonio)butanoate.

The fat (hydrophobic) material can be fatty acids and derivatives thereof which can include, but are not limited to, saturated and unsaturated fatty acids, odd and even number fatty acids, cis and trans isomers, and fatty acid derivatives including alcohols, esters, anhydrides, hydroxy fatty acids and prostaglandins. Saturated and unsaturated fatty acids that can be used include, but are not limited to, molecules that have between 12 carbon atoms and 22 carbon atoms in either linear or branched form. Examples of saturated fatty acids that can be used include, but are not limited to, lauric, myristic, palmitic, and stearic acids. Examples of unsaturated fatty acids that can be used include, but are not limited to, lauric, physeteric, myristoleic, palmitoleic, petroselinic, and oleic acids. Examples of branched fatty acids that can be used include, but are not limited to, isolauric, isomyristic, isopalmitic, and isostearic acids and isoprenoids. Fatty acid derivatives include 12-(((7'-diethylaminocoumarin-3yl)carbonyl)methylamino)-octadecanoic acid; N-[12-(((7'diethylaminocoumarin-3-yl)carbonyl)methyl-amino)octadecanoyl]-2-aminopalmitic acid, N succinyl-dioleoylphosphatidylethanol amine and palmitoyl-homocysteine; and combinations thereof. Mono, di and triglycerides or derivatives thereof that can be used include, but are not limited to, molecules that have fatty acids or mixtures of fatty acids between 6 and 24 carbon atoms, digalactosyldiglyceride, 1,2-dioleoyl-sn-glycerol; 1,2-cdipalmitoyl-sn-3 succinylglycerol; and 1,3-dipalmitoyl-2-succinylglycerol.

The triggered release system of the present invention is a dispersion formed of oil absorbing polymer nanospheres comprising sensory markers, and other various active ingredients, surrounded, encapsulated and coated by a surface active moisture sensitive polymer. The controlled release system of the present invention is characterized by: (i) protection of the active ingredients, as well as the volatile constituents of fragrances, during storage, until needed; (ii) moisture triggered controlled release of the fragrances, and other active ingredients; and (iii) prolonged release of fragrances, and other active ingredients over an extended period of time.

The oil-absorbing polymer nanospheres of the present invention have an average particle diameter that ranges from 20 nm to 1000 nm.

The invention further provides a process for preparing the triggered release system comprising the steps of:
  (a) adding one or more active ingredients into a dispersion of one or more oil absorbing polymers; or heating the dispersion to above the melting temperature of the hydrophobic materials;
  (b) heating one or more hydrophobic materials to a temperature above the melting point of the materials to form a melt and dissolving the sensory markers or active ingredients into the melt and adding the melt into the hot oil absorbing polymer dispersion; and
  (c) mixing the oil absorbing dispersion under high shear homogenization until a homogeneous dispersion is obtained.

The incorporation of oil absorbing dispersions including fragrances, other sensory markers and other active ingredients encapsulated within the oil absorbing nanospheres into cosmetic, personal care, and household formulations was found to provide fragrance "burst" in response to moisture. Furthermore the system was found to extend the release rate of the fragrances, and the active ingredients over an extended period of time.

Some embodiments of the invention are described in detail in the following Examples. All ratios, parts and percentages are expressed by weight unless otherwise specified, and all reagents used are of good commercial quality unless otherwise specified.

Suitable fragrance ingredients for encapsulation in the controlled release system of the present invention are naturally, or synthetically, derived fragrance ingredients which have low water solubility as determined by a calculated $\log_{10} P$, P being the n-octanol-water partition coefficient of the fragrance ingredient.

The ClogP of many perfume ingredients has been reported; for example, the Pomona92 database, available from Daylight Chemical Information Systems, Inc. (Daylight CIS), Irvine, Calif., contains many, along with citations to the original literature. However the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Volume 4, C. Hansch, P. G. Sammens, J. B. Taylor and C. A. Ramsden, editors, page 295, Pergamon Press, 1990, incorporated by reference herein). The fragment approach is based on the chemical structure of each perfume ingredient and takes into account the numbers and types of atoms, the atom connectivity and the chemical bonding. The ClogP values, which are the most reliable and widely used estimates for this physiochemical property, are preferably used instead of the experimental logP values in the selection of fragrance ingredients which are useful in the present invention.

Preparation of an OAL Fragrance Controlled Release System

EXAMPLE 1

50 grams of OAL dispersion comprising 50% solids (CS-31) are mixed with 50 grams of a floral fragrance. 100 grams of a polyvinyl alcohol solution comprising 30% solids is added to the OAL-fragrance mixture. The final encapsulated fragrance controlled release system created has 25% fragrance.

Incorporation of the Controlled Release System in Body Spray

EXAMPLE 2

The performance of a alcoholic body spray comprising the fragrance controlled release system of Example 1 (i.e., (i.e., the ability to yield a high impact fragrance "burst" upon perspiration and ability to prolong the perception of the fragrance on the skin over an extended period of time) was evaluated and compared to the performance of the same product comprising the neat fragrance, at the same fragrance level. The body spray base was ethanol.

The body sprays were prepared at a 1% effective concentration using the fragrance controlled release systems of Example 1. The control sample was prepared by weighting into a jar 1 gram of the fragrance and 99 grams of ethanol. The body spray comprising the controlled release system of the present invention (Example 1) is prepared by weighting 96 grams of ethanol into a jar following by adding 4 grams of the mixture of Example 1 following by mixing the solution.

Evaluation of Product Performance—Long Lasting Deodorancy

EXAMPLE 3

The body spray samples were applied on the forearm. The ability of the products to provide long lasting fragrance sensation was evaluated 2 hour after application of the product.

At all evaluation points, the skin area treated with the product comprising the fragrance controlled release system of the present invention were found to provide higher odor intensity compared to the control sample comprising the neat. Odor perception is, by its nature, a very subjective determination. According to the procedure, the samples to be tested are provided to a panel of six odor specialists who independently rank the odor intensity on a scale of 1 (least) to 10 (most) for odor and intensity. Samples yielding an odor ranking below about 2 possess an odor which would hardly be noticed by the general public.

The sensory data were as follow:

|  | Time After Application 2 Hours |
|---|---|
| Neat fragrance (Control) | 2 |
| Encapsulated fragrance | 6 |

These results show that the forearm treated with the control sample, comprising the neat fragrance, had very odor intensity 2 hours after application. The forearm treated with the sample comprising the encapsulated fragrance had higher odor intensity. Thus, the controlled release system of the present invention sustains the release rate of the fragrance over an extended period of time.

Evaluation of Product Performance—Moisture Triggered Controlled Release

EXAMPLE 4

The ability of the controlled release system of the present invention to provide fragrance "burst" was evaluated one hour after application of the product by misting the area with water. The products comprising the controlled release system of the present invention was found to provide high impact fragrance "burst" upon wetting the area whereas the control sample comprising the neat oil did not.

Incorporation of the Controlled Release System in an Underarm Deodorant Product

EXAMPLE 5

The fragrance controlled release system of Example 1 was incorporated in an antiperspirant gel formulation (Happi Magazine Formulary April 2000).

| Antiperspirant Gel Formulation | |
|---|---|
| Ingredients: | % Wt. |
| Phase A | |
| Abil EM 97 (Goldschmidt) (dimethicone copolyol (and) cyclopentasiloxane) | 2.40 |
| Abil B 8839 (Goldschmidt) (cyclopentasiloxane (and) cyclohexasiloxane) | 13.80 |
| Tegosoft (Goldschmidt) (isopropyl palmitate) | 0.50 |
| Dimethicone | 0.80 |
| Abil AV 20 (Goldschmidt) (phenyl trimethicone) | 0.50 |
| Abil B 8832 (Goldschmidt) (dimethicone copolyol) | 0.80 |
| Tegosoft SH (Goldschmidt) (stearyl heptanoate) | 0.75 |
| Phase B | |
| Aluminum chlorohydrate (50% solution) | 50.00 |
| SD Alcohol 40 | 4.00 |
| Sorbitol | 0.50 |

| -continued | |
|---|---|
| Antiperspirant Gel Formulation | |
| Ingredients: | % Wt. |
| Propylene glycol | 13.95 |
| 4 grams of f encapsulated fragrance of Example 1, or 1 gram of neat fragrance - Control | |
| Water | 5.00 |
| Colored wax micro spheres of Example 3 | 3.00 |
| Preservative | q.s. |

Procedure

Combine phase A ingredients, mixing to uniformity at room temperature. Add phase B ingredients in separate container, mixing to uniformity. The active salt should be mixed to a clear colorless solution. Measure the refractive indices of both phases. Adjust phase B using propylene glycol to raise, or water to lower, the refractive index of phase B to match that of phase A. The refractive indices should agree to the fourth decimal place for total clarity. Slowly stream phase B into phase A with slow (300 rpm) multiblade mixing. The addition rate should match the agitation, not allowing the water to pool on the emulsion surface. After the addition of the water phase is complete, increase the agitation rate to 1,200 rpm for a few minutes. This will build the viscosity of the mixture to a low viscosity flowing gel. Homogenize the mixture at a low rate. Mix until a firm gel is obtained. The wax micro spheres are added to the final product with slow mixing.

Evaluation of Product Performance—Long Lasting Deodorancy

EXAMPLE 6

The deodorant samples were applied on the forearm. The ability of the products to provide long lasting fragrance sensation was evaluated 4 hour after application of the product.

At all evaluation points, the skin area treated with the product comprising the fragrance controlled release system of the present invention were found to provide higher odor intensity compared to the control sample comprising the neat. Odor perception is, by its nature, a very subjective determination. According to the procedure, the samples to be tested are provided to a panel of six odor specialists who independently rank the odor intensity on a scale of 1 (least) to 10 (most) for odor and intensity. Samples yielding an odor ranking below about 2 possess an odor which would hardly be noticed by the general public.

The sensory data were as follow:

|  | Time After Application 4 Hours |
|---|---|
| Neat fragrance (Control) | 2 |
| Encapsulated fragrance | 5 |

These results show that the forearm treated with the control sample, comprising the neat fragrance, had very odor intensity 4 hours after application. The forearm treated with the sample comprising the encapsulated fragrance had higher odor intensity. Thus, the controlled release system of the present invention sustains the release rate of the fragrance over an extended period of time.

Evaluation of Product Performance—Moisture Triggered Controlled Release

EXAMPLE 7

The ability of the controlled release system of the present invention to provide moisture triggered controlled release or fragrance "burst" upon perspiration was evaluated 2 hours after application of the product on the forearm by misting the treated area with water. The products comprising the controlled release system of the present invention was found to provide high impact fragrance "burst" upon wetting the area whereas the control sample comprising the neat oil had very low odor intensity.

Incorporation of the Controlled Release System in a Lotion

EXAMPLE 8

The fragrance controlled release system of Example 1 was incorporated in a hand and body lotion formulation (Happi Magazine Formulary April 2003).

| Ingredients: | % Wt. |
|---|---|
| Phase A | |
| Carbopol Ultrez 10 (BASF) (carbomer) | 0.40 |
| Deionized water | 75.35 |
| Phase B | |
| Jeechem HPIB (Jeen) (dimethicone crosspolymer-3 (and) cyclomethicone (and) hydrogenated polyisobutene) | 8.00 |
| Jeecide G-II (Jeen) (diazolidinyl urea (and) methylparaben (and) propylparaben (and) propylene glycol) | 1.00 |
| Cucumber Extract (Jeen) (Botanicals Plus) (cucumber (and) propylene glycol) | 1.00 |
| Phase C | |
| Stearic Acid XXX (Jeen) (stearic acid) | 3.50 |
| Cetyl Alcohol (Jeen) (cetyl alcohol) | 1.00 |
| Stearyl Alcohol (Jeen) (stearyl alcohol) | 1.50 |
| Phase D | |
| Finsolv TN (Fintex) (C12–15 alkyl benzoate) | 7.00 |
| TEA 99% (Jeen) (triethanolamine) | 1.00 |
| Cucumber Melon (AFF) (fragrance) | 0.25 |

Procedure: Combine phase A ingredients with mixing and heat to 80° C. until dispersed and uniform. Add phase B ingredients, mixing until dispersed. Separately heat phase C ingredients with proper mixing to 75° C. Add phase C to phase A/B with mixing. Add phase D and mix until ambient temperature. The lotion samples were prepared at a 2% effective concentration using the fragrance controlled release systems of Example 1. The control sample was prepared by weighting into a jar 2 gram of the fragrance and 98 grams of the lotion base prepared. The body lotion comprising the controlled release system of the present invention (Example 1) is prepared by weighting 92 grams of ethanol into a jar following by mixing 8 grams of the mixture of Example 1 into the body lotion base prepared.

Evaluation of Fragrance Longevity on Skin Treated with the Body Lotion

EXAMPLE 9

The body lotion samples were applied on the forearm. The ability of the products to provide long lasting fragrance sensation was evaluated 2 hour after application of the product.

At all evaluation points, the skin area treated with the product comprising the fragrance controlled release system of the present invention were found to provide higher odor intensity compared to the control sample comprising the neat. Odor perception is, by its nature, a very subjective determination. According to the procedure, the samples to be tested are provided to a panel of six odor specialists who independently rank the odor intensity on a scale of 1 (least) to 10 (most) for odor and intensity. Samples yielding an odor ranking below about 2 possess an odor which would hardly be noticed by the general public.

The sensory data were as follow:

| | Time After Application 2 Hours |
|---|---|
| Neat fragrance (Control) | 3 |
| Encapsulated fragrance | 7 |

These results show that the forearm treated with the control sample, comprising the neat fragrance, had lower odor intensity 2 hours after application. The forearm treated with the sample comprising the encapsulated fragrance had higher odor intensity. Thus, the controlled release system of the present invention sustains the release rate of the fragrance over an extended period of time.

Evaluation of Product Performance—Moisture Triggered Controlled Release

EXAMPLE 10

The ability of the controlled release system of the present invention to provide moisture triggered release, or fragrance "burst" upon perspiration was evaluated 3 hours after application of the product by misting the area with water. The products comprising the controlled release system of the present invention was found to provide high impact fragrance "burst" upon wetting the area whereas the control sample comprising the neat oil had very low odor intensity in response to moisture:

Odor intensity after misting the forearm with water (3 hours after application)

| Neat fragrance (Control) | 2 |
|---|---|
| Encapsulated fragrance | 5 |

We claim:

1. A system for releasing one or more active ingredients from a composition comprising one or more oil absorbing polymers and a coating comprising one or more water sensitive, surface active polymers; wherein the active ingredients are encapsulated using a combination of (a) incorporating at least one active ingredient comprising fragrances in nano-particles using at least one oil absorbing polymer, wherein the oil absorbing polymer comprises a terpolymer comprising polymerized monomer units of (meth)acrylic acid, $C_8$-$C_{20}$ alkyl (meth) acrylate, and $C_1$-$C_{24}$ alkyl (meth)acrylate; and (b) encapsulating the nano-particles using at least one water sensitive, surface active polymer selected from the group consisting of polyvinyl pyrrolidone, water soluble celluloses, polyvinyl alcohol, ethylene maleic anhydride copolymer, methylvinyl ether maleic anhydride copolymer, acrylic acid copolymers, anionic polymers of methacrylic acid and methacrylate, cationic polymers including dimethyl-aminoethyl ammonium functional groups, polyethylene oxides, water soluble polyamides, water soluble polyesters and combinations thereof;

and are released upon contact of the coating with water.

2. The system according to claim 1, wherein the terpolymer includes from 80% to 98% by weight of a combination of $C_4$-$C_{24}$ alkyl (meth)acrylates and from 0.01% to 20% by weight of one or more ionic monomers selected from acrylic acid and methacrylic acid.

3. The system according to claim 1, wherein the oil absorbing polymers are in the form of nanospheres.

4. The system according to claim 1, wherein the active ingredient further comprises: oils, oil soluble compounds, water soluble compounds, water insoluble compounds, hydrophobic compounds, flavors, fabric softeners, bleaches, detergents or combinations thereof.

5. The system according to claim 1, wherein one or more hydrophobic materials are further incorporated in the oil absorbing polymer and are selected from the group consisting of: natural waxes, regenerated waxes, synthetic food waxes, animal waxes, beeswax, vegetable waxes, carnauba, candelilla, sugar cane, rice bran, bayberry wax, mineral waxes, petroleum waxes, paraffin waxes, and microcrystalline waxes, lipids, mono-, di and triglycerides, phospholipids, sphingolipids, cholesterol and steroid derivatives, terpenes, vitamins, solid hydrogenated castor oil, vegetable oils, hard fats, triglycerides of food grade purity, animal fats, vegetable oils, soy oils, and mixtures thereof.

* * * * *